(12) United States Patent
Iyer

(10) Patent No.: US 10,918,685 B2
(45) Date of Patent: Feb. 16, 2021

(54) HERBAL TOPICAL COMPOSITION FOR MUSCLE AND JOINT HEALTH, RECOVERY FROM EXERTION, AND FOR PAIN MANAGEMENT

(71) Applicant: Ravi Ramamoorthy Iyer, Herndon, VA (US)

(72) Inventor: Ravi Ramamoorthy Iyer, Herndon, VA (US)

(*) Notice: Subject to any disclaimer, the term of this patent is extended or adjusted under 35 U.S.C. 154(b) by 364 days.

(21) Appl. No.: 15/852,768

(22) Filed: Dec. 22, 2017

(65) Prior Publication Data

US 2018/0185429 A1 Jul. 5, 2018

Related U.S. Application Data

(60) Provisional application No. 62/442,609, filed on Jan. 5, 2017.

(51) Int. Cl.

| | | |
|---|---|---|
| *A61K 36/61* | (2006.01) | |
| *A61K 31/12* | (2006.01) | |
| *A61K 36/47* | (2006.01) | |
| *A61K 47/44* | (2017.01) | |
| *A61K 31/125* | (2006.01) | |
| *A61K 36/534* | (2006.01) | |
| *A61K 36/324* | (2006.01) | |
| *A61K 9/08* | (2006.01) | |
| *A61K 36/67* | (2006.01) | |
| *A61K 36/81* | (2006.01) | |
| *A61K 36/54* | (2006.01) | |
| *A61K 36/9066* | (2006.01) | |
| *A61K 47/10* | (2017.01) | |
| *A61K 31/165* | (2006.01) | |
| *A61K 31/4525* | (2006.01) | |
| *A61K 31/11* | (2006.01) | |
| *A61K 9/00* | (2006.01) | |
| *A61P 21/00* | (2006.01) | |
| *A61K 9/06* | (2006.01) | |
| *A61P 29/00* | (2006.01) | |

(52) U.S. Cl.
CPC ............ *A61K 36/61* (2013.01); *A61K 9/0014* (2013.01); *A61K 9/06* (2013.01); *A61K 9/08* (2013.01); *A61K 31/11* (2013.01); *A61K 31/12* (2013.01); *A61K 31/125* (2013.01); *A61K 31/165* (2013.01); *A61K 31/4525* (2013.01); *A61K 36/324* (2013.01); *A61K 36/47* (2013.01); *A61K 36/534* (2013.01); *A61K 36/54* (2013.01); *A61K 36/67* (2013.01); *A61K 36/81* (2013.01); *A61K 36/9066* (2013.01); *A61K 47/10* (2013.01); *A61K 47/44* (2013.01); *A61P 21/00* (2018.01); *A61P 29/00* (2018.01)

(58) Field of Classification Search
CPC .............. A61K 2300/00; A61K 36/324; A61K 36/534; A61K 36/54; A61K 36/67; A61K 36/9066; A61K 36/47; A61K 36/61; A61K 36/81; A61K 31/11; A61K 31/12; A61K 31/125; A61K 31/165; A61K 31/4525; A61K 47/10; A61K 47/44; A61K 9/0014; A61K 9/08; A61K 9/06; A61P 19/00; A61P 19/02; A61P 21/00; A61P 21/02; A61P 29/00

See application file for complete search history.

(56) References Cited

U.S. PATENT DOCUMENTS

| | | | |
|---|---|---|---|
| 9,415,019 B2* | 8/2016 | Alonso Fernandez | ..................... A61K 31/713 |
| 2014/0023703 A1* | 1/2014 | Alonso Fernandez | ..................... A61K 31/337 424/452 |

OTHER PUBLICATIONS

Federal Register vol. 44 No. 234, Food and Drug Administration (FDA), Dec. 4, 1979, pp. 69609-69916.
The Iyer Clinic Report, Avomeen Analytical Services, Oct. 31, 2017, 14 pages.

* cited by examiner

*Primary Examiner* — Aaron J Kosar

(57) ABSTRACT

A topical liniment composition that boost muscle relaxation, increase blood flow, and increase cutaneous delivery of herbal extract that contains polyphenols derived from red chili, black pepper, cinnamon, and turmeric includes a quantity of castor-mineral oil-camphor solution, a quantity of *eucalyptus* oil, a quantity of clove oil, a quantity of peppermint oil, a quantity of frankincense oil, a quantity of herbal extract concentrate solution, and a quantity of castor oil. Aforementioned ingredients are heterogeneously mixed with each other to formulate the topical liniment composition at standard temperature and pressure (STP). Additionally, a quantity of petroleum jelly and a quantity of beeswax can be heterogeneously mixed with the topical liniment composition to formulate the topical balm composition.

17 Claims, 7 Drawing Sheets

Topical liniment composition
- Castor-mineral oil-camphor solution
- Eucalyptus oil
- Clove oil
- Peppermint oil
- Frankincense oil
- Herbal extract concentrate solution
- Castor oil

FIG. 1

HERBAL TOPICAL COMPOSITION FOR MUSCLE AND JOINT HEALTH, RECOVERY FROM EXERTION, AND FOR PAIN MANAGEMENT

The current application claims a priority to the U.S. Provisional Patent application Ser. No. 62/442,609 filed on Jan. 5, 2017.

FIELD OF THE INVENTION

The present invention relates generally to the composition of a proprietary topical composition designed to boost muscle relaxation, increase blood flow, and increase cutaneous delivery of a proprietary herbal extract containing polyphenols from several herbs that have historical muscle wellness, analgesic, and antioxidant properties into target areas of muscles, ligaments, or joints.

BACKGROUND OF THE INVENTION

It is estimated that by the year 2017, Americans will spend about nearly $35 billion on pain management therapies. With respect to the $35 billion, approximately 25% or $8.75 billion is estimated to be in the area of musculoskeletal and low back pain, 20% or $7.0 billion in postoperative pain, 17% or $5.95 billion in cancer pain, 16% or $5.6 billion in neuropathic pain, and 22% or $7.7 billion in other transient pain conditions. With advancing average age of the general population, there has also been an increased focus on the maintenance of an active lifestyle with involvement in sports and weekend athletic activity in an effort to maintain health and vitality. It is now increasingly recognized that toxic effects of reactive radicals generated as a byproduct of normal metabolism as well as an effect of injury are a major cause of the process of aging and functional decline. It is also recognized that micro-injuries to muscles, ligaments, and joints constitute the normal burden of activities of daily living. The rate of these micro-injuries increases with both age and the activity level of the individual and the cumulative effect of this process is what constitute aging at the tissue level. But aging like all processes can be manipulated and tweaked to maximize functional lifespan. Apart from the genetics of the individual, some modifiable factors are critical in slowing down this aging process such as blood flow to target tissues. More specifically, any tissue that receives increased blood flow heals faster, functions better, and retains vitality longer. In this regard application of specialized pre-exercise muscle warm-up liniment immediately before the commencement of exercise or a post-exercise liniment to target muscle and joint areas in the golden hour after intense exercise rapidly promotes muscle recovery as well as joint elasticity and vitality. The ideal pre-or-post exercise liniment functions in 3 ways. (i) They rapidly penetrate the target muscle area and promote increased blood flow and deliver critical antioxidants that reduce toxic radical stress and damage at the microscopic level; (ii) They relax and soothe tight muscles and ligaments; (iii) They decrease pain and restore mobility.

With regards to pre-or-post exercise liniment, there has been growing interest and use of a variety of herbal preparations that have been shown to have significant beneficial effect on activating the toxic-radical neutralization pathways of the body. These herbal molecules belong to a heterogenous family of molecules known as polyphenols and by and large share a common chemical structural architecture characterized by the presence of large multiples of phenol structural units. While the biologic properties with regard to wellness and protection from injury has undergone resurgent interest, polyphenols are by no means new, and herbal polyphenols have been used in the tanning industry for centuries. The health promoting benefits of pomegranate juices, olives, tomatoes, grapes, ginger, turmeric, cinnamon, black pepper, and red chili pepper are now recognized to be in large part due to the polyphenols that these botanical sources contain. Of special interest is the recent recognition that the herbal extracts of turmeric, cinnamon, black pepper, and red chili pepper contain polyphenols (curcumin, cinnamaldehyde, piperine, capsacin respectively) that activate the genetic pathways that regulate the expression of the toxic radical scavenging system of Superoxide dismutase, Catalase, Glutathione reductase and DNA repair mechanisms at a cellular level. In general, the biochemical effects of these polyphenols have been described following oral ingestion and in a few cases on topical application (in the case of curcumin).

It is therefore for an objective of the present invention to provide a topical composition to boost muscle relaxation, increase blood flow, and increase cutaneous delivery of a proprietary herbal extract containing polyphenols. There exists a need for a muscle, ligament and joint liniment that would allow for rapid penetration of selected herbal polyphenols, essential oils and related extracts with known increased blood flow, anti-inflammatory, analgesic, muscle relaxing and soothing properties into a target body area through the medium of topical absorption. The presentation of these agents as a liniment or balm has the added advantage of allowing for use in the context of manual therapeutic massage of the musculoskeletal structure. However, these very same agents may also be delivered to a target musculoskeletal area through a topical adhesive patch, through occlusive or non-occlusive dressings, through electromotive force driven transdermal delivery systems, through nanoparticle delivery systems or liposomal delivery systems.

BRIEF DESCRIPTION OF THE DRAWINGS

FIG. 1 is a block diagram illustrating ingredients of the topical liniment composition.

DETAIL DESCRIPTIONS OF THE INVENTION

All illustrations of the drawings are for the purpose of describing selected versions of the present invention and are not intended to limit the scope of the present invention.

Figure 6:
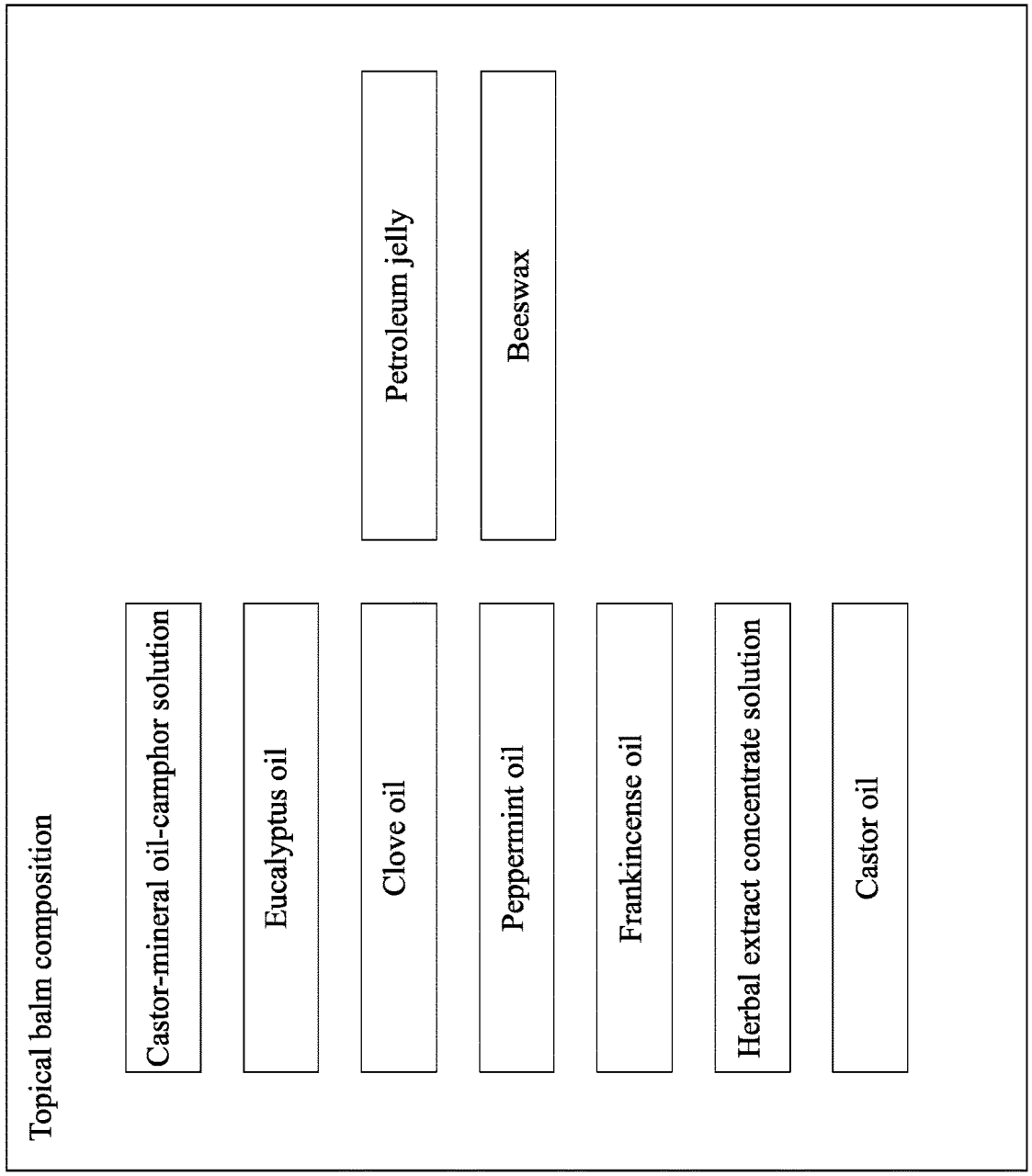
FIG. 6 is a block diagram illustrating ingredients of the topical balm composition.

The present invention is a topical composition is prepared from several herbs that have historical muscle wellness, analgesic, and antioxidant properties. The present invention boosts muscle relaxation, increase blood flow, and increase cutaneous delivery of herbal extract that contains polyphenols into a target area of muscle, ligament or joint for the relief of muscle strain, sprains and ligament and soft-tissue injuries. In reference to FIG. 1, the present invention comprises a quantity of castor-mineral oil-camphor solution, a quantity of *eucalyptus* oil, a quantity of clove oil, a quantity of peppermint oil, a quantity of frankincense oil, a quantity of herbal extract concentrate solution, and a quantity of castor oil. More specifically, castor-mineral oil-camphor solution is capable of providing muscle relaxation properties and analgesic properties. *Eucalyptus* oil can provide anti-inflammatory and analgesic properties. Clove oil is capable of providing vasoactive properties. Peppermint oil can provide muscle relaxation, increase blood flow, and pleasing odor. Frankincense oil is capable of providing anti-inflammatory properties. The quantity of herbal extract concentrate solution provides variety of medical befits such as, vasoactive, analgesic, and anti-inflammatory. Castor oil functions as the base ingredient within the present invention and provides rapid penetration through the dermal barrier. As a result, Castor oil acts as an efficient vehicle for the transdermal delivery of other biologic compounds of the present invention that may have poor penetration on their own. The quantity of castor-mineral oil-camphor solution, the quantity of *eucalyptus* oil, the quantity of clove oil, the quantity of peppermint oil, the quantity of frankincense oil, the quantity of herbal extract concentrate solution, and the quantity of castor oil are heterogeneously mixed with each other to formulate a topical liniment composition of the present invention. Additional ingredients, a quantity of petroleum jelly and a quantity of beeswax, can be heterogeneously mixed with the topical liniment composition to formulate a topical balm composition of the present invention as shown in FIG. 6.

Figure 2:
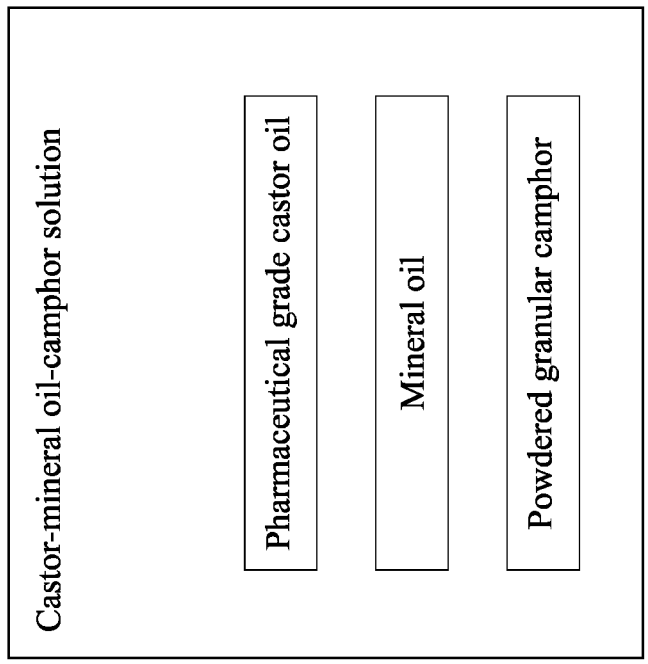
FIG. 2 is a block diagram illustrating ingredients of the castor-mineral oil-camphor solution for the topical liniment composition.

Castor oil, a vegetable oil that is obtained by pressing the seeds of castor oil plants, is an emollient solvent with rapid dermal penetration and contains mild muscle relaxing and mild analgesic properties. Due to the rapid penetration, castor oil functions as an efficient carrier vehicle for other biologic compounds of the present invention. Camphor is found from the wood of evergreen trees also known as cinnamonum *camphora*. Camphor functions as analgesic means, muscle relaxation means, and rubefacient (increases blood flow) means while providing a pleasing odor that is generally described as soothing or cooling. Camphor is recognized by the Food and Drug Administration (hereinafter FDA) in their Over-the-counter (OTC) Monograph as published in the Federal Register Vol. 44 No. 234 (Pgs. 69768-69866); Dec. 4, 1979 Subpart B (Section 348.10) as a CATEGORY I agent, ie., "External analgesic active ingredients that stimulate cutaneous sensory receptors (counter-irritants) and are safe and effective at the established concentrations and not misbranded for the indication". More specifically the FDA lists Camphor as a Category I (B) agent that "produces cooling and/or warming sensations which stimulate the skin and provide organoleptic properties". The concentrations approved by the FDA for OTC use ranges from 3-11% w/v dissolved in either mineral oil or petroleum jelly or phenol. In reference to FIG. 2 and FIG. 4, the quantity of camphor in the castor-mineral oil-camphor solution ranges between 8% to 10%, weight to volume (w/v) of the topical liniment composition at standard temperature and pressure (STP). In order to prepare the quantity of castor-mineral oil-camphor solution, a quantity of pharmaceutical grade castor oil, a quantity of mineral oil, and a quantity of powdered granular camphor are heterogeneously mixed with each other until all of the quantity of powdered granular camphor is completely dissolved. More specifically, about 500 milliliters (ml) of the quantity of pharmaceutical grade castor oil at STP and about 100 milliliters of the quantity of mineral oil (ml) at STP are placed in a 3-liter jar. Then, about 100 grams (g) of the quantity of powdered granular camphor at STP is added to the quantity of pharmaceutical grade castor oil and gently warmed with continuous stirring on a heated magnetic stirrer until all the camphor has completely dissolved. Once the quantity of powdered granular camphor dissolves within the quantity of pharmaceutical grade castor oil/mineral oil mix, the quantity of castor-mineral oil-camphor solution can be attained in order to proceed to the next phase of the overall formulation for the present invention.

*Eucalyptus* oil, which is extracted from leaves of selected *eucalyptus* through the steam distilled process has wide applications, such as analgesic means, anti-inflammatory properties, rubefacient (increases blood flow) means, antiseptic, and pleasing odor. *Eucalyptus* oil is recognized by the FDA in their OTC Monograph as published in the Federal Register Vol. 44 No. 234 (Pgs. 69768-69866); Dec. 4, 1979 Subpart B (Section 348.10) as a CATEGORY I agent, ie., "External analgesic active ingredients that stimulate cutaneous sensory receptors (counter-irritants) and are safe and effective at the established concentrations and not misbranded for the indication". More specifically the FDA lists *Eucalyptus* oil as a Category I (B) agent that "produces cooling and/or warming sensations which stimulate the skin and provide organoleptic properties". The concentrations approved by the FDA for OTC use ranges from 0.5-3% v/v. In reference to FIG. 4, the quantity of *eucalyptus* oil ranges between 2.5% to 3% volume to volume (v/v) of the topical liniment composition at STP.

Clove oil is an essential oil that is extracted from buds, leaf, and stems of the clove plant also known as syzygium *aromaticum*. The clove oil provides vasoactive, analgesic, and effective neuroanalgesic properties. Clove oil has not been listed by the FDA in their OTC Monograph as published in the Federal Register Vol. 44 No. 234 (Pgs. 69768-69866); Dec. 4, 1979 Subpart B (Section 348.10) as a CATEGORY I agent, ie., "External analgesic active ingredients" and as such this represents a unique use of this ingredient in the context of the present invention. In reference to FIG. 4, the quantity of clove oil ranges between 2% v/v to 4% v/v of the topical liniment composition at STP.

Peppermint oil, extracted from peppermint trees, has the ability to provide analgesic, muscle relaxation, and rubefacient (increases blood flow) properties while providing a pleasing odor that is generally described as soothing or cooling. Peppermint oil and its active ingredient menthol is recognized by the FDA in their OTC Monograph as published in the Federal Register Vol. 44 No. 234 (Pgs. 69768-69866); Dec. 4, 1979 Subpart B (Section 348.10) as a CATEGORY I agent, ie., "External analgesic active ingredients that stimulate cutaneous sensory receptors (counter-irritants) and are safe and effective at the established concentrations and not misbranded for the indication". More specifically the FDA lists Peppermint oil or Menthol as a Category I (B) agent that "produces cooling and/or warming sensations which stimulate the skin and provide organoleptic properties". The concentrations approved by the FDA for OTC use ranges from 1.25-16% v/v. In reference to FIG. 4, the quantity of peppermint oil ranges between 2.5% v/v to 5% v/v of the topical liniment composition at STP.

Frankincense oil, extracted from resin from the boswellia carteri trees, has the ability to provide anti-inflammatory properties, muscle relaxation properties, and a pleasing odor. Frankincense oil has not been listed by the FDA in their OTC Monograph as published in the Federal Register Vol. 44 No. 234 (Pgs. 69768-69866); Dec. 4, 1979 Subpart B (Section 348.10) as a CATEGORY I agent, ie., "External analgesic active ingredients" and as such this represents a unique use of this ingredient in the context of the present invention. In reference to FIG. 4, the quantity of frankincense oil ranges between 0.5% v/v to 1.5% v/v of the topical liniment composition at STP.

Figure 3:
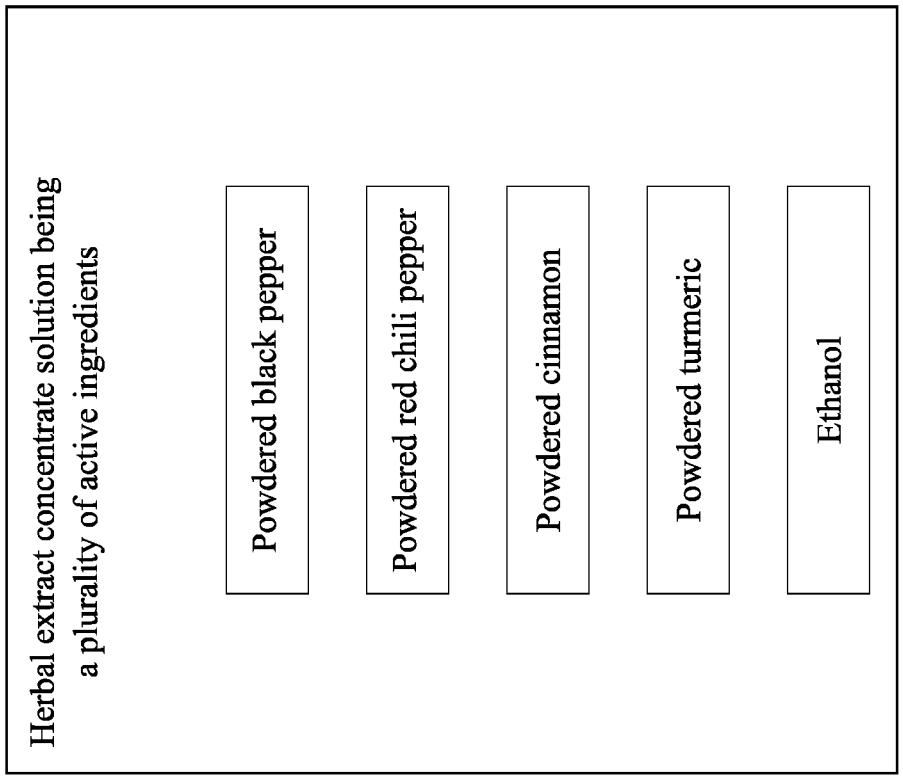
FIG. 3 is a block diagram illustrating ingredients of the herbal extract concentrate solution for the topical liniment composition.
Figure 4:
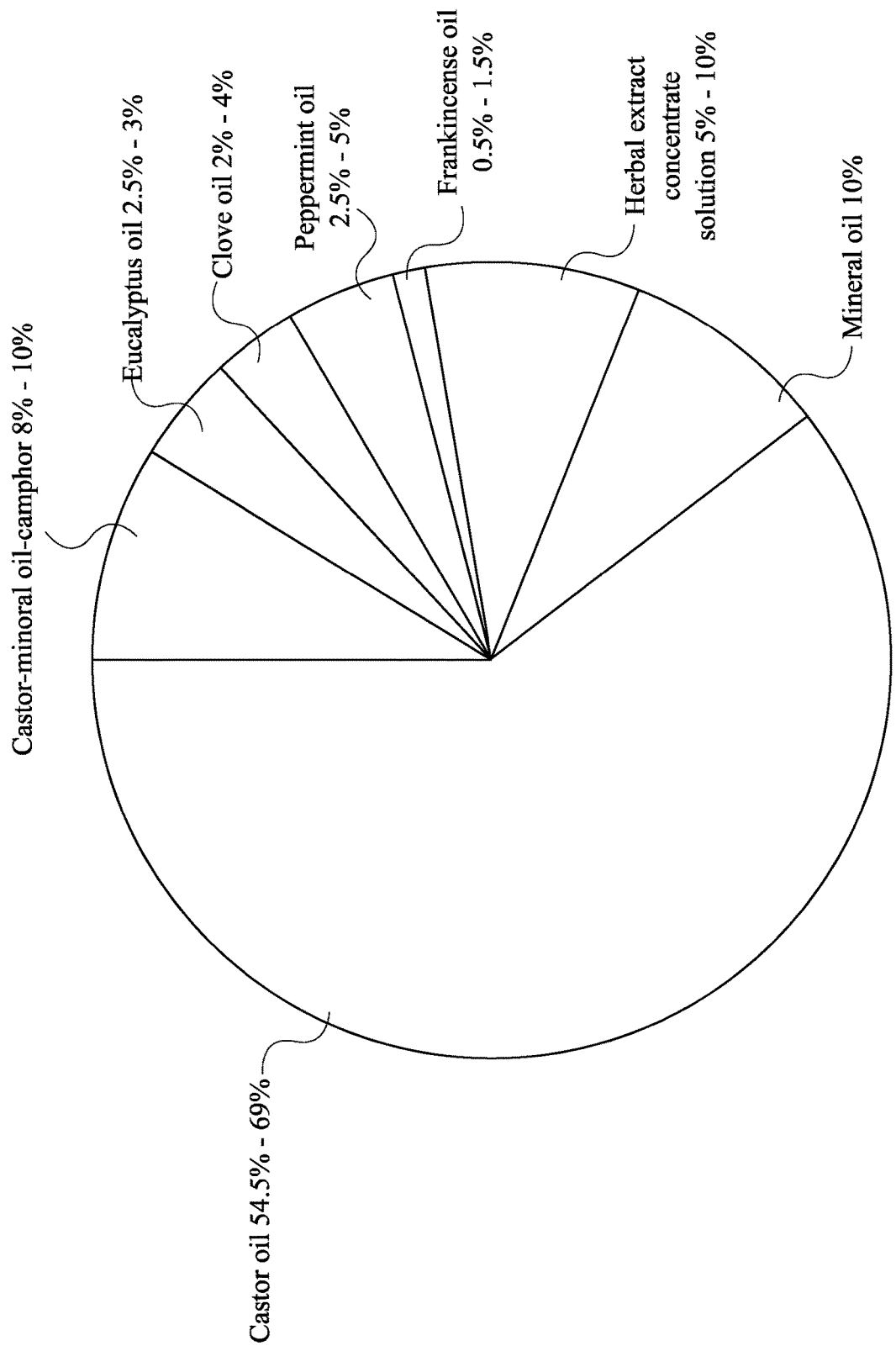
FIG. 4 is a chart illustrating percentage ranges for ingredients of the topical liniment composition.

In reference to FIG. 4, the quantity of herbal extract concentrate solution ranges between 5% v/v to 10% v/v of the topical liniment composition at STP. The quantity of herbal extract concentrate solution, which combines vasoactive, analgesic, and anti-inflammatory medical properties. The quantity of herbal extract concentrate solution is formulated from a plurality of active ingredients that includes a quantity of powdered black pepper, a quantity of powdered red chili pepper, a quantity of powdered cinnamon, a quantity of powdered turmeric, and a quantity of ethanol as shown in FIG. 3. More specifically, the quantity of powdered black pepper, the quantity of powdered red chili pepper, the quantity of powdered cinnamon, the quantity of powdered turmeric, and the quantity of ethanol are heterogeneously mixed with each other to formulate the quantity of herbal extract concentrate solution. More specifically, about 100 g of the quantity of powdered black pepper, about 100 g of the quantity of powdered red chili pepper, about 100 g of the quantity of powdered cinnamon, about 60 g of the quantity of powdered turmeric, and about 1000 ml of the quantity of ethanol are hermetically sealed within 3-liter capacity glass jars. Then, the glass jars are shaken on an orbital shaker at 100 revolutions per min at STP conditions for about 24 hours to formulate an ethanol-herbal slurry. The ethanol-herbal slurry is then vacuum filtered through a vacuum filtration apparatus across qualitative grade filter paper (preferably 9-centimeter diameter and medium 102) to recover herbal-ethanol extract that contains a complex mixture of the herbal polyphenols and oils. A residue of the herbal powder retained on the filter paper is re-suspended in an additional 500 ml of 95% v/v ethanol in the same 3-liter capacity glass jar and re-shaken for another 24 hours in the orbital shaker at 100 revolutions per min and STP conditions. This second ethanol-herbal slurry is again vacuum filtered through a vacuum filtration apparatus to extract another batch of herbal-ethanol extract that may contain any secondary residual herbal essences. The residual herbal powder retained on the filter paper is then discarded as waste. This process generally yields approximately 1200 ml of dark reddish brown herbal-ethanol extract that contains combined herbal essences, oils, and polyphenols from the quantity of powdered black pepper, the quantity of powdered red chili pepper, the quantity of powdered cinnamon, and the quantity of powdered turmeric. This dilute dark reddish brown herbal-ethanol extract normally carries an extremely pungent odor, which is readily appreciable to the nose.

The 1200 ml of herbal-ethanol extract is then concentrated by simple distillation via retort and ice-water condensation apparatus. More specifically, herbal-ethanol extract is gently warmed in a boiling flask in a heating mantle with continuous magnetic stirring. As a result, the ethanol distills off at 78° Celsius and after condensation is recovered in the condensate recovery flask. This distillation process is continued until the original 1200 ml of herbal-ethanol extract has reduced in volume to approximately 400 ml thus representing three-fold concentration of herbal-ethanol extract. This 3× concentrate represents herbal-ethanol extract mother liqueur and is stored at ambient temperature until further use. The quantity of herbal extract concentrate solution includes the following herbal extracts and properties as the herbal extracts work well with respective described ingredients of the present invention.

Figure 5:
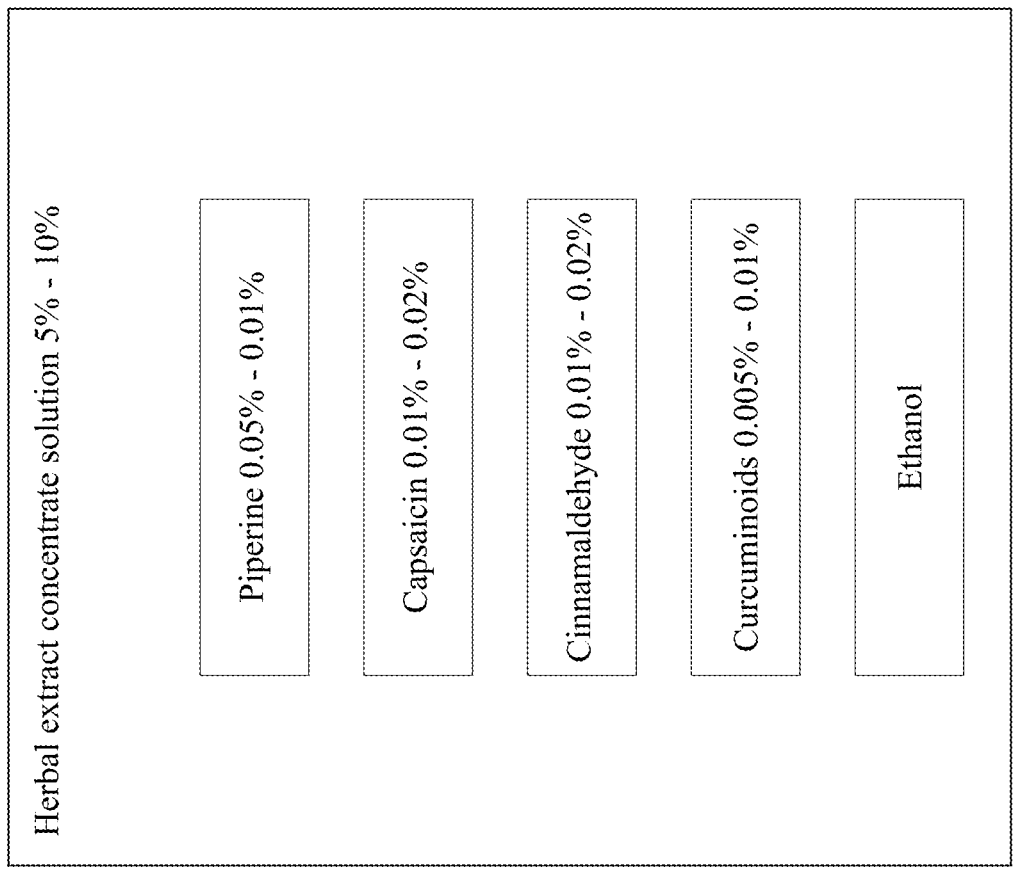
FIG. 5 is a block diagram illustrating the properties of the herbal extract concentrate solution and the respective percentage ranges within the topical liniment composition.

Capsaicin: Vasoactive, analgesic, anti-inflammatory properties and activates cellular toxic radical defense system. Synergizes with camphor, clove oil, peppermint, and *eucalyptus* oils. Capsaicin, *Capsicum* and *Capsicum* oleoresin are recognized by the FDA in their OTC Monograph as published in the Federal Register Vol. 44 No. 234 (Pgs. 69768-69866); Dec. 4, 1979 Subpart B (Section 348.10) as a CATEGORY I agent, ie., "External analgesic active ingredients that stimulate cutaneous sensory receptors (counter-irritants) and are safe and effective at the established concentrations and not misbranded for the indication". More specifically the FDA lists Capsaicin, *Capsicum* and *Capsicum* oleoresin as a Category I (D) agent that "produces irritation without rubefaction although equal in potency to Group I9A) agents". The concentrations approved by the FDA for OTC use ranges from 0.025-0.25% v/v. In reference to FIG. 4-5, a quantity of Capsaicin ranges between 0.010-0.020% w/v in the topical liniment composition, and is based upon the primary Capsacinoid peaks eluting approximately at 29.584 minutes and 30.308 minutes on a Luna 5 u C18 100A, 150×4.6 millimeters (mm) High-performance liquid chromatography (HPLC) column with detection at UV 221 nanometers (nm) as shown in the HPLC plot of the Capsaicin concentration in the herbal extract by Avomeen Analytical Services (technical report attached to this filing by way of reference; page 12) and is actually less than the FDA approved amount for this ingredient.

In addition to these two primary Capsacinoid peaks identified in the quantity of herbal extract concentrate solution, there are 16 additional minor Capsacinoid peaks that are identified in the quantity of herbal extract concentrate solution that may also constitute biologically active ingredients in the topical liniment composition. These minor Capsacinoid peaks are seen eluting approximately at 1.414 min, 2.039 min, 2.878 min, 3.521 min, 14.085 min, 18.830 min, 27.428 min, 28.894 min, 31.695 min, 32.255 min, 32.494 min, 34.056 min, 36.157 min, 36.765 min, 38.370 min, and 39.034 min on a Luna 5 u C18 100A, 150×4.6 mm HPLC column with detection at UV 221 nm as shown in the HPLC plot of the quantity of herbal extract concentrate solution by Avomeen Analytical Services (Reference: Avomeen Analytical Services technical report; Page 12.)

Piperine: Vasoactive, analgesic, anti-inflammatory properties and activates cellular toxic radical defense system. Directly increases penetration of curcumin. Synergizes with camphor, clove oil, peppermint, and *eucalyptus* oils. Piperine is not recognized by the FDA in their OTC Monograph as published in the Federal Register Vol. 44 No. 234 (Pgs. 69768-69866); Dec. 4, 1979 Subpart B (Section 348.10) as an "External analgesic active ingredients that stimulate cutaneous sensory receptors (counter-irritants) and are safe and effective at the established concentrations and not misbranded for the indication". The use of Piperine as an ingredient in the topical liniment composition is therefore a unique application. In reference to FIG. 4-5, a quantity of Piperine ranges between 0.050-0.10% w/v in the topical liniment composition, and is based upon the primary Piperinoid peaks eluting approximately at 29.461 min and 29.336 min on a Luna 5 u C18 100A, 150×4.6 mm HPLC column with detection at UV 345 nm as shown in the HPLC plot of the quantity of herbal extract concentrate solution in the analysis of the Piperine concentration in the quantity of herbal extract concentrate solution by Avomeen Analytical Services (technical report attached to this filing by way of reference; Page 8).

In addition to these two primary Piperinoid peaks identified in the quantity of herbal extract concentrate solution, there are 5 additional minor Piperinoid peaks that are identified in the quantity of herbal extract concentrate solution that may also constitute biologically active ingredients in the topical liniment composition. These minor Piperinoid peaks are seen eluting approximately at 23.729 min, 26.228 min, 27.151 min, 31.442 min, and 32.237 min on a Luna 5 u C18 100A, 150×4.6 mm HPLC column with detection at UV 345 nm as shown in the HPLC plot of the quantity of herbal extract concentrate solution in the analysis of the Piperine concentration in the quantity of herbal extract concentrate solution (Reference Avomeen Analytical Services technical report; Page 8)

Curcumin,
Bisdemothxycurcumin,
Demothxycurcumin
Collectively listed as
"Curcuminoids": Vasoactive, analgesic, anti-inflammatory properties and activates cellular toxic radical defense system. Synergizes with piperine, camphor, clove oil, peppermint, and *eucalyptus* oils. Curcuminoids are not recognized by the FDA in their OTC Monograph as published in the Federal Register Vol. 44 No. 234 (Pgs. 69768-69866); Dec. 4, 1979 Subpart B (Section 348.10) as an "External analgesic active ingredients that stimulate cutaneous sensory receptors (counter-irritants) and are safe and effective at the established concentrations and not misbranded for the indication". The use of Curcuminoids as an ingredient in the topical liniment composition is therefore a unique application. In reference to FIG. 4-5, a quantity of Curcuminoids ranges between 0.005-0.01% w/v in the topical liniment composition, and is based upon the 3 primary curcuminoid peaks eluting approximately at 8.533 min, 9.122 min, and 9.723 min on a Luna 5 u C18 100A, 150×4.6 mm HPLC column with detection at UV 420 nm as shown in the HPLC plot of the quantity of herbal extract concentrate solution by Avomeen Analytical Services in the analysis of the Curcuminoid concentration in the herbal extract by Avomeen Analytical Services (technical report attached to this filing by way of reference; Page 10).

In addition to these three primary Curcuminoid peaks identified in the quantity of herbal extract concentrate solution, there are 7 additional minor Curcuminoid peaks that are identified in the quantity of herbal extract concentrate solution that may also constitute biologically active ingredients in the topical liniment composition. These minor curcuminoid peaks are seen eluting approximately at 1.013 min, 1.120 min, 1.624 min, 2.189 min, 6.790 min, 7.724 min, 11.698 min, 12.150 min, and 13.248 min. on a Luna 5 u C18 100A, 150×4.6 mm HPLC column with detection at UV 420 nm as shown in the HPLC plot of the quantity of herbal extract concentrate solution by Avomeen Analytical Services (Reference Avomeen Analytical Services technical report; Page 10)

Cinnamaldehyde: Vasoactive, analgesic, anti-inflammatory properties and activates cellular toxic radical defense system. Synergizes with camphor, clove oil, peppermint, and *eucalyptus* oils. Cinnamaldehyde is not recognized by the FDA in their OTC Monograph as published in the Federal Register Vol. 44 No. 234 (Pgs. 69768-69866); Dec. 4, 1979 Subpart B (Section 348.10) as an "External analgesic active ingredients that stimulate cutaneous sensory receptors (counter-irritants) and are safe and effective at the established concentrations and not misbranded for the indication". The use of Cinnamaldehyde as an ingredient in the topical liniment composition is therefore a unique application. In reference to FIG. 4-5, a quantity of Cinnamaldehyde ranges between 0.01-0.02% w/v in the topical liniment composition, and is based upon the 3 primary Cinnamaldehyde peaks eluting approximately at 18.831 min, 21.914 min, and 29.582 min on a Luna 5 u C18 100A, 150×4.6 mm HPLC column with detection at UV 280 nm as shown in the HPLC plot of the quantity of herbal extract concentrate solution by Avomeen Analytical Services in the HPLC plot of the analysis of the Cinnamaldehyde concentration in the herbal extract by Avomeen Analytical Services (technical report attached to this filing by way of reference; Page 6).

In addition to these three primary Cinnamaldehyde peaks identified in the herbal extract, there are 16 additional minor Cinnamonoid polyphenol peaks that are identified in the herbal extract that may also constitute biologically active ingredients in the topical liniment composition. These minor Cinnamonoid polyphenol peaks are seen eluting approximately at 1.482 min, 2.090 min, 3.519 min, 14.083 min, 20.343 min, 27.427 min, 28.361 min, 28.888 min, 31.694 min, 32.499 min, 33.321 min, 34.937 min, 36.765 min, 37.553 min, 39.035 min, and 41.649 min. on a Luna 5 u C18 100A, 150×4.6 mm HPLC column with detection at UV 280 nm as shown in the HPLC plot of the quantity of herbal extract concentrate solution by Avomeen Analytical Services in the HPLC plot of the analysis of the Cinnamaldehyde concentration in the quantity of herbal extract concentrate solution by Avomeen Analytical Services (Reference Avomeen Analytical Services technical report; Page 6)

In reference to FIG. 4, the quantity of mineral oil is at 10% v/v while castor oil ranges between 54.5% v/v to 69% v/v of the topical liniment composition at STP as the quantity of castor oil is added to make the final volume of the topical liniment composition to 1-liter batch. The use of mineral oil is to act as an approved solvent for camphor. Castor oil is selected as the base ingredient due to following reasons within the present invention.

a) Castor oil is evaluated by the FDA as a GRASE (Generally Regarded as Safe and Effective) chemical.
b) Castor oil rapidly penetrates the dermal barrier and in doing so acts as an efficient vehicle for the transdermal delivery of other biologic compounds which may have poor penetration on their own.
c) Castor oil has mild to moderate muscle relaxation and analgesic properties.
d) Castor oil has excellent emollient effects on the skin yielding a direct cosmetic advantage.

Figure 7:
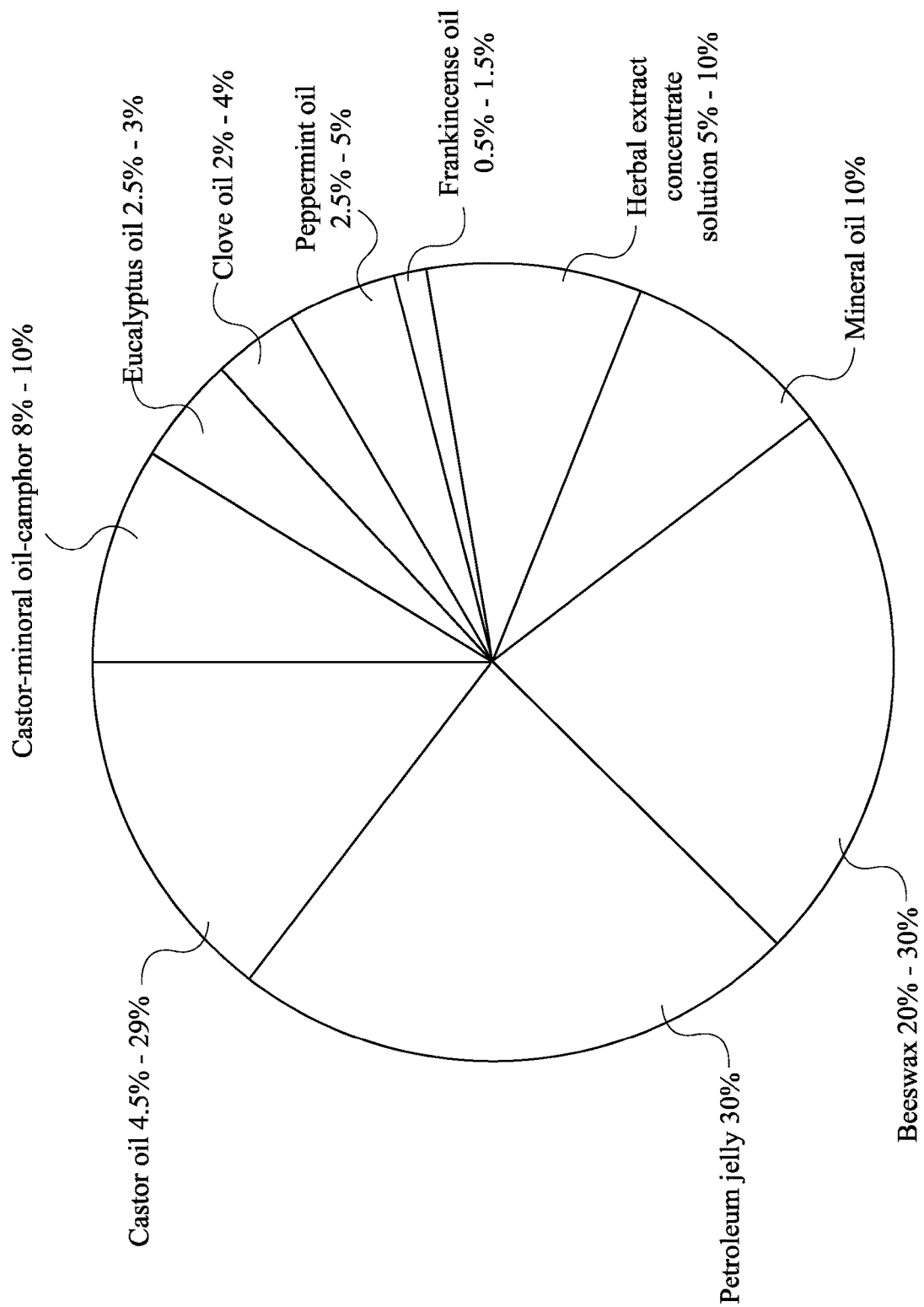
FIG. 7 is a chart illustrating percentage ranges for ingredients of the topical balm composition.

In reference to FIG. 6-7, the quantity of petroleum jelly ranges about 30% w/v of the topical balm composition at STP. Petroleum jelly functions as a base ingredient and as a moisture insulator for tissue dehydration within the topical balm composition, maximizing the benefits of the present invention. The quantity of beeswax ranges between 20% w/v to 30% w/v of the topical balm composition at STP. Bees wax works well within the present invention because it contains compounds called wax esters, which keeps skin hydrated. Bees wax can also be helpful as an ultraviolet light inhibitor and as a skin conditioner. Bees wax has special characteristics such as plasticity and compatibility that allow it to produce a pleasant scent when mixed with other ingredients of the present invention. Due to the addition of the quantity of petroleum jelly and the quantity of beeswax, the quantity of castor oil differs within the topical balm composition at STP in comparison to the topical liniment composition at STP. In other words, the quantity of castor oil ranges between 4.5% v/v to 29% v/v of the topical balm composition at STP as the quantity of castor oil is added to make the final volume of the topical balm composition to 1-liter batch.

The present invention provides maximum relief in the case of muscle and soft-tissue injury but is also appreciable when applied to arthritic joints. Another highly effective application of the present invention is in cases of neuropathic pain where the degree of relief is excessive. In an exemplary clinical use, approximately 40,000 applications of the liniment in muscle strains and muscle spasm has produced no adverse effect and uniformly produced dramatic amelioration of pain and discomfort within 30 minutes of application. It is pertinent to note that the combined use of the polyphenols Capsaicin, Piperine, Cinnamaldehyde and Curcuminoids appears to allow efficacious results at lower concentrations of each without the risk of adverse effects. One of the restrictions on the OTC use of Capsaicin for the relief of pain has been the need to reduce the risk of skin irritation that can happen at higher concentrations of Capsaicin. The FDA limits the range of Capasicin concentrations in OTC preparations to 0.025-0.25% and preparations with concentrations higher than 0.25% are restricted to use under the prescribing authority of a medical professional. Accordingly, the presently available OTC analgesics and pain relief preparations contain Capsaicin concentrations between 0.1-0.25% primarily to ensure the maximal allowable availability of potency within the established boundaries of safety. The concentration of Capsaicin in the present invention is between 0.01 to 0.02% while the efficacy based upon clinical use is equal or superior to existing OTC preparations with no adverse effect reported in over exemplary 40,000 applications. The novelty of the present invention therefore appears to reside in the combinatorial use of capsaicin along with extracts of black pepper, cinnamon and turmeric. This combinatorial use allows for efficacy at lower concentrations of each agent while also securing the benefit of minimization of adverse effects. The present invention represents the topical liniment composition and the topical balm composition for human use. Another version of the same liniment and balm with varying ratios of the same ingredients can also be optimized and tested as a canine liniment and as an equine liniment for muscle wellness and recovery after intense exertion with very favorable results.

Although the invention has been explained in relation to its preferred embodiment, it is to be understood that many other possible modifications and variations can be made without departing from the spirit and scope of the invention as hereinafter claimed.

What is claimed is:

1. A topical composition to boost muscle relaxation, increase blood flow, and increase cutaneous delivery of herbal extract that contains polyphenols comprises:
   a quantity of castor-mineral oil-camphor solution;
   a quantity of *eucalyptus* oil;
   a quantity of clove oil;
   a quantity of peppermint oil;
   a quantity of frankincense oil;
   a quantity of herbal extract concentrate solution;
   a quantity of castor oil; and
   the quantity of castor-mineral oil-camphor solution, the quantity of *eucalyptus* oil, the quantity of clove oil, the quantity of peppermint oil, the quantity of frankincense oil, the quantity of herbal extract concentrate solution, and the quantity of castor oil being heterogeneously mixed into a topical liniment composition.

2. The topical composition to boost muscle relaxation, increase blood flow, and increase cutaneous delivery of herbal extract that contains polyphenols as claimed in claim 1 comprises:
   the quantity of castor-mineral oil-camphor solution being about 8% to 10% (w/v) in the topical liniment composition at standard temperature and pressure (STP).

3. The topical composition to boost muscle relaxation, increase blood flow, and increase cutaneous delivery of herbal extract that contains polyphenols as claimed in claim 2 comprises:
   a quantity of pharmaceutical grade castor oil;
   a quantity of mineral oil;
   a quantity of powdered granular camphor; and
   the quantity of pharmaceutical grade castor oil, the quantity of mineral oil, and the quantity of powdered granular camphor being heterogeneously mixed into the quantity of castor-mineral oil-camphor solution.

4. The topical composition to boost muscle relaxation, increase blood flow, and increase cutaneous delivery of herbal extract that contains polyphenols as claimed in claim 3 comprises:
   the quantity of pharmaceutical grade castor oil being about 500 milliliters (ml) of the quantity of castor-mineral oil-camphor solution at STP;
   the quantity of mineral oil being about 100 ml of the quantity of castor-mineral oil-camphor solution at STP; and
   the quantity of powdered granular camphor being about 100 grams (g) of the quantity of castor-mineral oil-camphor solution at STP.

5. The topical composition to boost muscle relaxation, increase blood flow, and increase cutaneous delivery of herbal extract that contains polyphenols as claimed in claim 1 comprises:
   the quantity of *eucalyptus* oil being about 2.5% to 3% (v/v) in the topical liniment composition at STP.

6. The topical composition to boost muscle relaxation, increase blood flow, and increase cutaneous delivery of herbal extract that contains polyphenols as claimed in claim 1 comprises:
   the quantity of clove oil being about 2% to 4% (v/v) in the topical liniment composition at STP.

7. The topical composition to boost muscle relaxation, increase blood flow, and increase cutaneous delivery of herbal extract that contains polyphenols as claimed in claim 1 comprises:
   the quantity of peppermint oil being about 2.5% to 5% (v/v) in the topical liniment composition at STP.

8. The topical composition to boost muscle relaxation, increase blood flow, and increase cutaneous delivery of herbal extract that contains polyphenols as claimed in claim 1 comprises:
the quantity of frankincense oil being about 0.5% to 1.5% (v/v) in the topical liniment composition at STP.

9. The topical composition to boost muscle relaxation, increase blood flow, and increase cutaneous delivery of herbal extract that contains polyphenols as claimed in claim 1 comprises:
the quantity of herbal extract concentrate solution being about 5% to 10% (v/v) in the topical liniment composition at STP.

10. The topical composition to boost muscle relaxation, increase blood flow, and increase cutaneous delivery of herbal extract that contains polyphenols as claimed in claim 9 comprises:
a plurality of active ingredients;
the plurality of active ingredients includes a quantity of powdered black pepper, a quantity of powdered red chili pepper, a quantity of powdered cinnamon, a quantity of powdered turmeric, and a quantity of ethanol; and
the quantity of powdered black pepper, the quantity of powdered red chili pepper, the quantity of powdered cinnamon, the quantity of powdered turmeric, and the quantity of ethanol being heterogeneously mixed into the quantity of herbal extract concentrate solution.

11. The topical composition to boost muscle relaxation, increase blood flow, and increase cutaneous delivery of herbal extract that contains polyphenols as claimed in claim 10 comprises:
the quantity of powdered black pepper being about 100 grams (g) of the quantity of herbal extract concentrate solution at STP;
the quantity of powdered red chili pepper being about 100 g of the quantity of herbal extract concentrate solution at STP;
the quantity of powdered cinnamon being about 100 g of the quantity of herbal extract concentrate solution at STP;
the quantity of powdered turmeric being about 60 g of the quantity of herbal extract concentrate solution at STP; and
the quantity of ethanol being about 1000 ml of the quantity of herbal extract concentrate solution at STP.

12. The topical composition to boost muscle relaxation, increase blood flow, and increase cutaneous delivery of herbal extract that contains polyphenols as claimed in claim 11 comprises:
a quantity of Piperine in the quantity of about 0.050-0.01% (w/v) in the topical liniment composition at STP;
a quantity of Capsaicin in the quantity of about 0.010-0.020% (w/v) in the topical liniment composition at STP;
a quantity of Cinnamaldehyde in the quantity of about 0.010-0.020% (w/v) in the topical liniment composition at STP; and
a quantity of Curcuminoids in the quantity of about 0.005-0.01% (w/v) in the topical liniment composition at STP.

13. The topical composition to boost muscle relaxation, increase blood flow, and increase cutaneous delivery of herbal extract that contains polyphenols as claimed in claim 1 comprises:
the quantity of castor oil being about 54.5% to 69% (v/v) in the topical liniment composition at STP, and the quantity of mineral oil being 10% v/v in the topical liniment composition at STP.

14. The topical composition to boost muscle relaxation, increase blood flow, and increase cutaneous delivery of herbal extract that contains polyphenols as claimed in claim 1 comprises:
a quantity of petroleum jelly;
a quantity of beeswax; and
the quantity of petroleum jelly and the quantity of beeswax being heterogeneously mixed together with the topical liniment composition to compose a topical balm composition.

15. The topical composition to boost muscle relaxation, increase blood flow, and increase cutaneous delivery of herbal extract that contains polyphenols as claimed in claim 14 comprises:
the quantity of petroleum jelly being about 30% (w/v) in the topical balm composition at STP.

16. The topical composition to boost muscle relaxation, increase blood flow, and increase cutaneous delivery of herbal extract that contains polyphenols as claimed in claim 14 comprises:
the quantity of beeswax being about 20% to 30% (w/v) in the topical balm composition at STP.

17. The topical composition to boost muscle relaxation, increase blood flow, and increase cutaneous delivery of herbal extract that contains polyphenols as claimed in claim 14 comprises:
the quantity of castor oil being about 4.5% to 29% (v/v) in the topical balm composition at STP.

* * * * *